United States Patent
Mizugaki et al.

(10) Patent No.: US 12,172,949 B2
(45) Date of Patent: Dec. 24, 2024

(54) METHOD FOR PRODUCING ALCOHOL

(71) Applicants: OSAKA UNIVERSITY, Suita (JP); DAICEL CORPORATION, Osaka (JP)

(72) Inventors: Tomoo Mizugaki, Suita (JP); Kiyotomi Kaneda, Suita (JP); Yasuteru Kajikawa, Tokyo (JP); Yuuichirou Hirai, Tokyo (JP)

(73) Assignees: OSAKA UNIVERSITY, Osaka (JP); DAICEL CORPORATION, Osaka (JP)

( * ) Notice: Subject to any disclaimer, the term of this patent is extended or adjusted under 35 U.S.C. 154(b) by 578 days.

(21) Appl. No.: 17/428,097

(22) PCT Filed: Sep. 17, 2019

(86) PCT No.: PCT/JP2019/036317
§ 371 (c)(1),
(2) Date: Aug. 3, 2021

(87) PCT Pub. No.: WO2020/166117
PCT Pub. Date: Aug. 20, 2020

(65) Prior Publication Data
US 2022/0024842 A1   Jan. 27, 2022

(30) Foreign Application Priority Data
Feb. 15, 2019 (JP) .................. 2019-025399

(51) Int. Cl.
| | | |
|---|---|---|
| C07C 29/149 | (2006.01) |
| B01J 21/06 | (2006.01) |
| B01J 23/42 | (2006.01) |
| B01J 23/652 | (2006.01) |
| B01J 37/02 | (2006.01) |

(52) U.S. Cl.
CPC ........... *C07C 29/149* (2013.01); *B01J 21/066* (2013.01); *B01J 23/42* (2013.01); *B01J 23/6525* (2013.01); *B01J 37/0201* (2013.01); *B01J 37/0205* (2013.01)

(58) Field of Classification Search
None
See application file for complete search history.

(56) References Cited

FOREIGN PATENT DOCUMENTS

| | | | |
|---|---|---|---|
| CN | 102553585 A | * | 7/2012 |
| JP | 2015-86199 A | | 5/2015 |
| JP | 2016-160243 A | | 9/2016 |

OTHER PUBLICATIONS

CN102553585a, machine translation, Jul. 11, 2012; pp. 1-17 (Year: 2012).*
International Preliminary Report on Patentability and Written Opinion mailed Aug. 26, 2021, in PCT/JP2019/036317.
International Search Report mailed Nov. 5, 2019, in PCT/JP2019/036317.
Mizugaki et al., "Development of High Performance Heterogeneous Catalysts for Selective Cleavage of C—O and C—C Bonds of Biomass-Derived Oxygenates," Chem. Rec. (2019), vol. 19, pp. 1179-1198.
Mizugaki et al., "Selective hydrogenation of levulinic acid to 1,4-pentanediol in water using a hyrdoxyapatite-supported-Pt-Mo bimetallic catalyst," Green Chemistry (2015), vol. 17, No. 12, pp. 5136-5139.

* cited by examiner

*Primary Examiner* — Medhanit W Bahta
(74) *Attorney, Agent, or Firm* — Birch, Stewart, Kolasch & Birch, LLP

(57) ABSTRACT

The present invention provides a method for selectively producing an alcohol by efficiently hydrogenating a lactone. The present invention is a method for producing an alcohol, the method including hydrogenating a substrate lactone represented by Formula (1), in the presence of a catalyst described below, to produce an alcohol that is represented by Formula (2).

In the formulae, R represents a divalent hydrocarbon group which may have a hydroxyl group.

The catalyst comprises:
  metal species including $M_1$ and $M_2$; and
  a support supporting the metal species, and
  wherein
  $M_1$ is rhodium, platinum, ruthenium, iridium, or palladium;
  $M_2$ is tin, vanadium, molybdenum, tungsten, or rhenium; and
  the support is hydroxyapatite, fluorapatite, hydrotalcite, or $ZrO_2$.

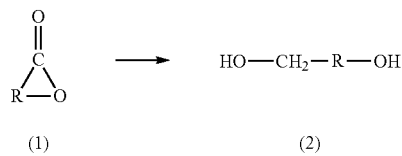

(1)                    (2)

11 Claims, No Drawings

METHOD FOR PRODUCING ALCOHOL

TECHNICAL FIELD

The present invention relates to a method for producing an alcohol by hydrogenating a lactone. The present application claims priority from the Japanese Patent Application JP 2019-025399 filed in Japan on Feb. 15, 2019, the contents of which are incorporated herein.

BACKGROUND ART

There is a strong need for the development of efficient conversion reactions for producing useful chemical products from biomass resources in order to reduce global carbon dioxide emissions. Known compounds derived from biomass include lactones such as γ-valerolactone. Alcohols formed by hydrogenating the lactones are useful as raw materials for chemical products such as plastics.

In the related art, reducing agents such as $LiAlH_4$ and $NaBH_4$ have been used in the reaction of hydrogenating lactones to produce alcohols. However, when these reducing agents are used, the reaction produces a large amount of salt as a by-product which remains after the reaction, which is problematic. Also, when using a method adopting the reducing agents, one has to go through complex reaction involving multiple steps prior to formation of an alcohol, which is burdensome. Therefore, there is a demand for the development of a catalytic hydrogenation reaction through which an alcohol can be easily produced by using molecular hydrogen, whose byproduct after the reaction is only water, as a reducing agent.

Regarding catalytic hydrogenation reactions of lactones using molecular hydrogen as a reducing agent, known methods include the ones using Ir—Ru—Re/activated carbon, Ir—Zr—Re/graphene, and the like as catalysts (Patent Document 1). However, in order to suppress the formation of by-products and selectively produce an alcohol, the reaction must be carried out under high temperature and high pressure. Also, the reaction was carried out in the presence of an organic solvent such as 1,2-dimethoxyethane.

CITATION LIST

Patent Document

Patent Document 1: JP 2015-86199 A

SUMMARY OF INVENTION

Technical Problem

It is therefore an object of the present invention to provide a method for selectively producing an alcohol by efficiently hydrogenating a lactone.

Another object of the present invention is to provide a method for selectively producing an alcohol by efficiently hydrogenating a lactone in a one-step manner.

Also, another object of the present invention is to provide a method for selectively producing an alcohol by efficiently hydrogenating a lactone using water as a solvent.

Yet another object of the present invention is to provide a method for selectively producing an alcohol by efficiently hydrogenating a lactone under mild conditions.

Further another object of the present invention is to provide a catalyst in applications to selectively produce an alcohol by efficiently hydrogenating a lactone.

Solution to Problem

As a result of diligent research to solve the problems described above, the inventors of the present invention discovered that a specific catalyst described below allows the rapid hydrogenation of a lactone to selectively produce an alcohol under mild conditions in a one-step manner while using water as a solvent. The present invention was completed based on these findings.

That is, the present invention provides a method for producing an alcohol, the method including hydrogenating a substrate lactone represented by Formula (1) to form an alcohol represented by Formula (2), in the presence of a catalyst, the catalyst comprises:
metal species including $M_1$ and $M_2$; and
a support supporting the metal species, and
wherein
$M_1$ is rhodium, platinum, ruthenium, iridium, or palladium;
$M_2$ is tin, vanadium, molybdenum, tungsten, or rhenium; and
the support is hydroxyapatite, fluorapatite, hydrotalcite, or $ZrO_2$.

[Chem. 1]

$$\underset{(1)}{\overset{R-O}{\underset{}{\bigtriangleup}}\!\!\!\!\overset{O}{\overset{\|}{C}}} \longrightarrow \underset{(2)}{HO-CH_2-R-OH}$$

(In the formula, R represents a divalent hydrocarbon group which may have a hydroxyl group)

The present invention also provides a method for producing the alcohol in which the catalyst contains $M_1$ and $M_2$ as metal species in a ratio of from 0.05 to 1 mol of $M_2$ per 1 mol of $M_1$.

The present invention also provides a method for producing the alcohol in which the amount of the catalyst in terms of the $M_1$ metal is from 0.01 to 30 mol % of the substrate.

The present invention also provides a method for producing the alcohol in which hydrogenation reaction is carried out in the presence of water.

The present invention also provides a catalyst comprising:
metal species including $M_1$ and $M_2$; and
a support supporting the metal species,
wherein:
$M_1$ is rhodium, platinum, ruthenium, iridium, or palladium;
$M_2$ is tin, vanadium, molybdenum, tungsten, or rhenium, and
the support is hydroxyapatite, fluorapatite, hydrotalcite, or $ZrO_2$,
wherein the catalyst being used to hydrogenate a lactone to form a corresponding alcohol.

Advantageous Effects of Invention

By the production method according to an embodiment of the present invention, an alcohol can be efficiently and selectively produced from a lactone under mild conditions and in a one-step manner.

In addition, by the production method according to an embodiment of the present invention, it is possible to efficiently and selectively produce an alcohol from a lactone using water, which is safe to the human body and environmentally friendly, as a solvent.

The alcohol thus produced is useful as a raw material for chemical products such as plastics. Therefore, the production method according to an embodiment of the present invention is useful as a method for producing alcohol industrially.

Furthermore, the $M_1$ and $M_2$ supported on the support according to an embodiment of the present invention can be suitably used as a catalyst (a solid catalyst or a heterogeneous catalyst) for hydrogenating a lactone to produce an alcohol while using water as a solvent.

DESCRIPTION OF EMBODIMENTS

Catalyst

In the method for producing an alcohol according to an embodiment of the present invention, at least one catalyst is used, the catalyst including $M_1$ and $M_2$ described below, which serve as metal species, supported on a support described below.

($M_1$): rhodium, platinum, ruthenium, iridium or palladium
($M_2$): tin, vanadium, molybdenum, tungsten or rhenium
(Support): hydroxyapatite, fluorapatite, hydrotalcite or $ZrO_2$ $M_1$ and $M_2$ that are supported on a support may be a simple metal, or may be a metal salt, a metal oxide, a metal hydroxide, a metal complex, or the like.

The amount of $M_1$ (in terms of metal) is, for example, approximately from 1 to 50 wt. %, preferably from 1 to 20 wt. %, and particularly preferably from 1 to 10 wt. %, of the weight of the support (100 wt. %). When the catalyst supports $M_1$ in an excess amount, the catalytic activity reaches saturation and levels off, and does not achieve the effect of promoting the reaction further. Meanwhile, when the catalyst supports $M_1$ in an amount less than the range described above, the catalyst may not readily exhibit sufficient catalytic activity.

The amount of $M_2$ (in terms of metal) is, for example, approximately from 0.01 to 20 wt. %, preferably from 0.01 to 10 wt. %, more preferably from 0.01 to 3 wt. %, even more preferably from 0.05 to 2 wt. %, particularly preferably from 0.1 to 1.5 wt. %, most preferably from 0.2 to 1.0 wt. %, especially preferably from 0.3 to 0.8 wt. %, of the weight of the support (100 wt. %). When the amount of $M_2$ is out of the range described above, it becomes difficult to efficiently hydrogenate the lactone, and alcohol yield tends to decrease.

Note that the amount of the metal species supported on the support can be measured by the ICP-AES method.

The catalyst in an embodiment of the present invention is considered to have an active site at the interface of $M_1$ and $M_2$. Furthermore, when either one of $M_1$ and $M_2$ is in excess, catalytic activity decreases, efficient hydrogenation of the lactone becomes difficult, and alcohol yield tends to decline; this may be because the metal species in excess covers the other metal species, reducing the interface and shrinking the active site.

Therefore, the amounts of $M_1$ and $M_2$ are preferably in a specific range, and the amount of $M_2$ per 1 mol of $M_1$ is preferably, for example, from 0.05 to 1 mol. Furthermore, the upper limit of the amount of $M_2$ per 1 mol of $M_1$ is preferably 0.8 mol, more preferably 0.6 mol, even more preferably 0.5 mol, and particularly preferably 0.4 mol. The lower limit of the amount of $M_2$ per 1 mol of $M_1$ is preferably 0.07 mol, more preferably 0.1 mol, particularly preferably 0.15 mol, most preferably 0.2 mol, and especially preferably 0.3 mol.

The catalyst according to an embodiment of the present invention may support metal species other than $M_1$ and $M_2$, but the amount of metal species other than $M_1$ and $M_2$ with respect to the total amount of $M_1$ and $M_2$ supported is, for example, 200 mol % or less, preferably 150 mol % or less, more preferably 100 mol % or less, further preferably 70 mol % or less, even further preferably 50 mol % or less, even further more preferably 30 mol % or less, particularly preferably 10 mol % or less, most preferably 5 mol % or less, and especially preferably 1 mol % or less. When the amount of metal species other than $M_1$ and $M_2$ exceeds the range described above, the effect of the present invention may not be readily achieved; this may be because the shrunken active site.

In an embodiment of the present invention, $M_1$ and $M_2$ are used while being supported on a support. Having $M_1$ and $M_2$ supported on a support can increase the interface area of $M_1$ and $M_2$, and thereby increasing exposure of the active site.

Furthermore, in an embodiment of the present invention, since a catalyst containing $M_1$ and $M_2$ which are supported on a support is used, the catalyst can be easily separated from the reaction products by physical separation methods such as filtration or centrifugation after completion of the reaction; the catalyst separated from the reaction products and recovered can be reused as it is, or after, for example, being washed or dried. In an embodiment of the present invention, since an expensive catalyst can be used repeatedly as described above, the cost of producing an alcohol can be greatly reduced.

The support is preferably hydroxyapatite or fluorapatite, particularly preferably hydroxyapatite, from the perspective that an alcohol can be selectively produced from a lactone at a high yield.

The support is preferably hydroxyapatite or hydrotalcite, particularly preferably hydroxyapatite, from the perspective that an alcohol can be selectively produced from a lactone at a high yield.

The support is preferably hydroxyapatite or $ZrO_2$, particularly preferably $ZrO_2$, from the perspective that an alcohol can be selectively produced from a lactone at a high yield.

For the hydroxyapatite, commercially available products such as the product with the trade name "Tricalcium Phosphate" (available from Wako Pure Chemical Industries, Ltd.) can be suitably used.

The catalyst can be suitably used as a hydrogenation catalyst (or cyclic ester group hydrogenation catalyst) for efficiently hydrogenating a lactone to form an alcohol using water as a solvent.

Method for Preparing Catalyst

The catalyst in an embodiment of the present invention can be prepared, for example, by an impregnation method.

An impregnating method is a method for supporting a metal species on a support, including immersing a support in a solution (for example, an aqueous solution) prepared by dissolving a compound containing the metal species mentioned above (i.e. a metal compound) in a solvent (for example, water), impregnating the support with the metal compound, and then subjecting to calcination. The supported amount of the metal species can be controlled by adjusting, for example, the concentration of the metal compound in the solution, or the immersion time of the support.

The catalyst in an embodiment of the present invention can be prepared by: a sequential impregnation method, in which a support is sequentially impregnated with a solution prepared by dissolving a compound containing $M_1$ in a solvent (hereinafter, it may be referred to as "$M_1$-containing solution") and a solution prepared by dissolving a compound containing $M_2$ in a solvent (hereinafter, it may be referred to as "$M_2$-containing solution"); or, a co-impregnation method in which a support is simultaneously impregnated with an $M_1$-containing solution and an $M_2$-containing solution. When preparing the catalyst using a co-impregnation method, calcination may be performed after impregnating the support in a mixed solution of an $M_1$-containing solution and an $M_2$-containing solution; meanwhile, when preparing the catalyst using a sequential impregnation method, it is preferable to perform calcination each time after immersing the support in an $M_1$-containing solution and an $M_2$-containing solution one after another.

Among these, in an embodiment of the present invention, a catalyst prepared by supporting $M_1$ and $M_2$ on a support by a co-impregnation method is particularly preferable from the perspective that an alcohol can be produced selectively.

For example, a catalyst in which Pt being $M_1$ and Mo being $M_2$ are supported on a support by the co-impregnation method (Pt—Mo/support) can be prepared by: immersing the support in a solution prepared by dissolving a Pt compound (such as $H_2PtCl_6$) and a Mo compound [such as $(NH_4)_6Mo_7O_{24}.4H_2O$] in water; then, retrieving the product from the solution and subjecting the product to calcination.

Among these, in an embodiment of the present invention, a catalyst prepared by supporting $M_1$ and $M_2$ on a support using a sequential impregnation method, and in particular, a catalyst prepared using a sequential impregnation method in which first $M_2$ and then $M_1$ is supported on a support, is preferable from the perspective of excellent catalytic activity and rapid progression of hydrogenation reaction of lactone.

For example, a catalyst in which Pt being $M_1$ and Mo being $M_2$ are supported on a support by the sequential impregnation method (Pt/Mo/support) can be prepared by: immersing the support in a solution prepared by dissolving a Mo compound [such as $(NH_4)_6Mo_7O_{24}.4H_2O$] in water; then, retrieving the product from the solution and subjecting to calcination to prepare Mo/support; immersing the resulting Mo/support in a solution prepared by dissolving a Pt compound (such as $H_2PtCl_6$) in water; then, retrieving the product from the solution and subjecting the product to calcination.

Compared to using the co-impregnation method, using the sequential impregnation method can allow the alloy of $M_1$ and $M_2$ be supported on the surface of the support while preventing $M_1$ from being covered by $M_2$ (or $M_2$ from being covered by $M_1$). The catalyst prepared in this manner can exhibit excellent catalytic activity due to highly dispersed nano-sized alloy of $M_1$ and $M_2$ supported on the surface of the support.

The temperature at which the support is immersed in the solution is, for example, approximately from 10 to 80° C.

The time of immersing the support in the solution is, for example, approximately from 1 to 30 hours, preferably from 1 to 5 hours.

Calcination is carried out by, for example, performing heating at from 300 to 700° C. for from 1 to 5 hours using a muffle furnace or the like.

Furthermore, reduction treatment may be further performed after calcination. Examples of reducing agents used for the reduction treatment include hydrogen ($H_2$).

The temperature and time of the reduction treatment are, for example, approximately from 0.5 to 5 hours (preferably from 0.5 to 2 hours) at a temperature of from 0 to 600° C. (preferably from 100 to 200° C.).

The catalyst prepared by the preparation method described above may then be subjected to, for example, a washing treatment (washing with water, an organic solvent, or the like), or a drying treatment (drying by vacuum drying, or the like).

Substrate

In an embodiment of the present invention, at least one lactone represented by Formula (1) below is used as a substrate.

[Chem. 2]

(1)

In the formula above, R represents a divalent hydrocarbon group which may have a hydroxyl group.

The divalent hydrocarbon group in R includes a divalent aliphatic hydrocarbon group, a divalent alicyclic hydrocarbon group, a divalent aromatic hydrocarbon group, and a divalent group formed by two or more groups selected from the aforementioned groups bonded together.

Examples of the divalent aliphatic hydrocarbon group include: straight-chain or branched alkylene groups having from 1 to 10 carbons (preferably from 1 to 5 carbons), such as a methylene group, a methylmethylene group, a dimethylmethylene group, an ethylene group, a propylene group, and a trimethylene group; and straight-chain or branched alkenylene groups having from 2 to 10 carbons (preferably 2 to 5 carbons), such as a vinylene group, a 1-methylvinylene group, a propenylene group, a 1-butenylene group, a 2-butenylene group, a 1-pentenylene group, and a 2-pentenylene group.

Examples of the divalent alicyclic hydrocarbon group include: cycloalkylene groups having from 3 to 10 carbons (preferably from 3 to 6 carbons), such as a cyclopentylene group, a cyclohexylene group (such as a 1,2-cyclohexylene group, a 1,3-cyclohexylene group, and a 1,4-cyclohexylene group), and a cycloheptylene group; and cycloalkenylene groups having from 3 to 10 carbons (preferably from 3 to 6 carbons), such as a cyclopropenylene group, a cyclobutenylene group, a cyclopentenylene group, a cyclohexenylene group, and a cyclooctenylene group.

Examples of the divalent aromatic hydrocarbon group include: arylene groups having from 6 to 20 carbons, such as a phenylene group (for example, an o-phenylene group, an m-phenylene group, and a p-phenylene group), a biphenylene group, a naphthylene group, a binaphthylene group, and an anthracenylene group.

Examples of the divalent group formed by two or more groups selected from the aforementioned hydrocarbon groups bonded together include: cyclohexylenebis(methylene) [for example, 1,2-cyclohexylenebis(methylene), 1,3-cyclohexylenebis(methylene), and 1,4-cyclohexylenebis(methylene)]; and phenylenebis(methylene) [for example, 1,2-phenylenebis(methylene), 1,3-phenylenebis(methylene), and 1,4-phenylenebis(methylene)].

The divalent hydrocarbon group may have a hydroxyl group as a substituent. Furthermore, the divalent hydrocarbon group may have a substituent other than hydroxyl group that is selected from, for example, a $C_{1-5}$ alkoxy group, a $C_{6-10}$ aryloxy group, a $C_{7-11}$ aralkyloxy group, an oxo group, a halogen atom, and a halo $C_{1-5}$ alkyl group.

Among these, as the substrate in an embodiment of the present invention, a lactone in which R in Formula (1) is a divalent aliphatic hydrocarbon group (especially preferably an alkylene group having from 1 to 10 carbons, most preferably an alkylene group having from 1 to 7 carbons) is preferable from the perspective that such lactone can be efficiently converted under mild conditions (with a conversion ratio of, for example, 95% or above).

The substrate in an embodiment of the present invention is preferably a lactone with a from 3- to 12-membered ring, particularly preferably a lactone with a from 3- to 10-membered ring, and more preferably a lactone with a from 3- to 7-membered ring, from the perspective that such lactone can be efficiently converted under mild conditions (with a conversion ratio of, for example, 95% or above).

Among these, a lactone other than γ-valerolactone is preferable as the substrate.

The substrate in an embodiment of the present invention is preferably a lactone selected from lactones with 3- to 4-membered rings and 6- to 10-membered rings, particularly preferably a lactone selected from lactones with 3-, 4-, and 6-membered rings, especially preferably a lactone with a 4-membered ring (such as β-Butyrolactone), from the perspective that the corresponding alcohol can be formed in a high yield (with the yield being, for example, 80% or above, preferably 85% or above) under mild conditions (for example, a temperature of below 150° C. and/or a hydrogen pressure of 6 MPa or less).

Method for Producing Alcohol

In the method for producing an alcohol according to an embodiment of the present invention, a lactone, which is the substrate, is hydrogenated (preferably hydrogenated with molecular hydrogen) in the presence of the aforementioned catalyst. In the method for producing an alcohol according to an embodiment of the present invention, the ring-opening reaction of the cyclic ester group contained in the lactone proceeds rapidly, and the corresponding alcohol (preferably polyol) is efficiently produced.

[Chem. 3]

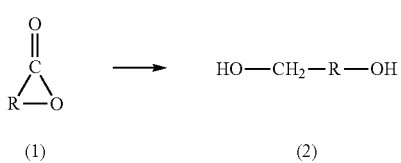

(1)　　　　　　　　　　(2)

(where R is the same as described above)

The amount of catalyst, in terms of the metal $M_1$ contained in the catalyst, is, for example, approximately from 0.01 to 30 mol %, preferably from 0.1 to 10 mol %, particularly preferably from 0.5 to 5 mol %, most preferably from 1 to 5 mol %, of the substrate.

Furthermore, the amount of the catalyst, in terms of the metal $M_2$ contained in the catalyst, is, for example, approximately from 0.01 to 10 mol %, preferably from 0.05 to 5 mol %, and particularly preferably from 0.1 to 2 mol %, of the substrate.

When the catalyst is used in the range described above, the substrate can be efficiently hydrogenated under mild conditions to selectively produce an alcohol. When the amount of the catalyst is less than the range described above, the alcohol yield tends to be reduced.

Hydrogen used for the hydrogenation reaction can be supplied by, for example, carrying out the reaction in a hydrogen atmosphere, or bubbling hydrogen gas.

In an embodiment of the present invention, the use of the catalyst mentioned above facilitates rapid hydrogenation of the cyclic ester group contained in the substrate under mild conditions. Hydrogen pressure during the hydrogenation reaction is, for example, not greater than 10 MPa, preferably not greater than 7 MPa, more preferably not greater than 6 MPa, and particularly preferably not greater than 5 MPa (such as from 1 to 5 MPa).

The reaction temperature of the hydrogenation reaction is, for example, from 50 to 200° C., preferably from 100 to 180° C., particularly preferably from 120 to 160° C., most preferably from 120 to 150° C., especially preferably from 120° C. to lower than 150° C.

The reaction time of the hydrogenation reaction is, for example, approximately from 1 to 36 hours, preferably from 5 to 30 hours, and particularly preferably from 5 to 20 hours.

In addition, the hydrogenation reaction can be performed by any method, such as a batch method, a semi-batch method, and a continuous method.

The hydrogenation reaction is preferably carried out in the liquid phase. In other words, the hydrogenation reaction according to an embodiment of the present invention is preferably a liquid-phase reaction. This is because lactone has a high boiling point, so when the hydrogenation reaction is carried out in the gas phase, reaction products tend to decompose and alcohol yield tends to decrease.

When the reaction is carried out in the liquid phase, examples of solvent include: water; alcohol-based solvents such as methanol, ethanol, 2-propanol, and 1-butanol; ether-based solvents such as 1,4-dioxane, THF, 1,2-dimethoxyethane, and diethyl ether; hydrocarbon solvents such as toluene, hexane, and dodecane; halogenated hydrocarbon solvents such as 1,2-dichloroethane and dichloromethane. One of these solvents can be used alone or two or more in combination.

Among these solvents, in an embodiment of the present invention, water is preferable from the perspective that it is safe to the human body and environmentally friendly. That is, the hydrogenation reaction in an embodiment of the present invention is preferably performed in the presence of water. In addition, in an embodiment of the present invention, when hydrogenation reaction is carried out in the presence of water, the ester ring-opening reaction of the lactone proceeds more rapidly, and the corresponding alcohol can be efficiently produced. Therefore, in an embodiment of the present invention, it is especially preferable that hydrogenation reaction is carried out in the presence of water from the perspective that alcohol can be produced at a high yield.

The amount of water used in the total amount of the solvent is, for example, not less than 1 wt. %, more preferably not less than 5 wt. %, more preferably not less than 10 wt. %, even more preferably not less than 30 wt. %, further more preferably not less than 50 wt. %, particularly preferably not less than 70 wt. %, most preferably not less than 80 wt. %, and especially preferably not less than 90 wt. %. Therefore, the amount of solvent used excluding water (for example, an organic solvent, particularly an ether-based solvent such as THF and 1,2-dimethoxyethane) in the total amount of the solvent is, for example, preferably not greater than 90 wt. %, more preferably not greater than 80 wt. %, even more preferably not greater than 70 wt. %, further preferably not greater than 50 wt. %, even further preferably not greater than 30 wt. %, particularly preferably not greater than 20 wt. %, more particularly preferably not greater than 10 wt. %, most preferably not greater than 5 wt. %, and especially preferably not greater than 1 wt. %.

The amount of solvent used excluding water (for example, an organic solvent, particularly an ether-based solvent such as THF and 1,2-dimethoxyethane) with respect to the amount of water used is preferably not greater than 100 wt. %, more preferably not greater than 70 wt. %, even more preferably not greater than 50 wt. %, further preferably not greater than 30 wt. %, particularly preferably not greater than 20 wt. %, more particularly preferably not greater than 10 wt. %, most preferably not greater than 5 wt. %, especially preferably not greater than 1 wt. %.

The amount of solvent used is preferably in a range such that the initial concentration of the substrate is, for example, approximately from 0.01 to 10 wt. % when reacted using a batch method.

In an embodiment of the present invention, since the catalyst described above is used, hydrogenation reaction of the substrate can proceed rapidly even if one or two or more selected from the followings does not exist in the reaction system: acids such as hydrochloric acid, sulfuric acid, phosphoric acid, and acetic acid, and bases such as sodium hydroxide, potassium hydroxide, sodium carbonate, sodium hydrogen carbonate, potassium carbonate, and potassium hydrogen carbonate. Also, in an embodiment of the present invention, although an acid or base mentioned above may be used, the amount used (the total amount when two or more are used) is preferably, for example, less than 0.001 mol per 1 mol of the substrate, and it is particularly preferable that none of the acids or bases is actually used. This is because when the acid or base mentioned above is present in the reaction system beyond the range described above, the post-treatment needs to include neutralization treatment, which produces salt as a by-product, and removing the by-produced salt causes loss of the product. Furthermore, the corrosiveness of the acids or bases mentioned above limits the material of the reactor to be used.

After the completion of the reaction, the resulting reaction products can be separated and purified by: a separation method, such as filtration, concentration, distillation, extraction, crystallization, recrystallization, and column chromatography; or a separation method in combination thereof.

The method for producing an alcohol according to an embodiment of the present invention facilitates efficient conversion of the substrate even under mild conditions. The conversion ratio of the substrate after 30 hours (preferably after 20 hours) from the start of the reaction is, for example, not less than 80%, preferably not less than 90%, and particularly preferably not less than 95%.

Furthermore, rapid hydrogenation of the cyclic ester group of the lactone, which is the substrate, facilitates the production of an alcohol selectively and at a high yield.

When the conversion ratio of the substrate reaches 90% or greater, the selectivity of the alcohol, represented by Formula (2) above, in the total amount of reaction products is, for example, not less than 70%, preferably not less than 75%, particularly preferably not less than 85%, and most preferably not less than 90%.

Therefore, with the method for producing an alcohol according to an embodiment of the present invention, a lactone can be efficiently hydrogenated to produce the corresponding alcohol selectively at a high yield in a simple one-step method while using water, which is safe to the human body and environmentally friendly, as a solvent.

EXAMPLES

Hereinafter, the present invention will be described more specifically with reference to examples, but the present invention is not limited by these examples.

Example 1 (Preparation of Catalyst: Co-Impregnation Method)

0.0898 g of $H_2PtCl_6$ and 0.088 g of $(NH_4)_6Mo_7O_{24} \cdot 4H_2O$ were dissolved in 50 mL of water to prepare a solution; 1 g of hydroxyapatite (HAP, trade name "Tricalcium Phosphate", available from Wako Pure Chemical Industries, Ltd.) was immersed in the resulting solution for 4 hours under room temperature (25° C.). After immersion, the hydroxyapatite was retrieved from the solution, and water was distilled off in a rotary evaporator under reduced pressure. This resulted in a powder. The produced powder was then calcined in an air atmosphere in a muffle furnace at 500° C. for 3 hours to prepare Catalyst (1) [Pt—Mo/HAP, amount of Pt supported: 4 wt. %, amount of Mo supported: 0.485 wt. %, Mo/Pt (molar ratio)=0.25].

Example 2

1 mmol of β-Butyrolactone serving as the substrate, 100 mg of catalyst (1) [Pt that is 2 mol % of the substrate, Mo that is 0.5 mol % of the substrate, in terms of metal], and 3 mL of water were charged in an autoclave having a Teflon (trade name) inner cylinder and reacted at 130° C. for 12 hours under the condition of hydrogen pressure of 5 MPa to form reaction products. The conversion ratio (cony. [%]) of the substrate was measured using HPLC, and the yield of each one of the reaction products was measured using a gas chromatograph mass spectrometer (GC-MS).

Examples 3 to 7

The same procedure as in Example 2 was performed except for changing the substrate, reaction temperature, and hydrogen pressure as described in the table below.

The results are summarized and shown in the table below.

TABLE 1

| Ex. | substrate | $H_2$ (MPa) | temp. (° C.) | conversion (%) | product yield (%) | |
|---|---|---|---|---|---|---|
| 2 | 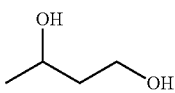 | 5 | 130 | >99 | 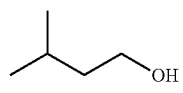 87 | 3 |

TABLE 1-continued

| Ex. | substrate | H₂ (MPa) | temp. (° C.) | conversion (%) | product yield (%) |
|---|---|---|---|---|---|
| 3 | 3-hydroxy-γ-butyrolactone | 5 | 120 | >99 | sec-butanol 8; 1,2,4-butanetriol 87; 1,4-butanediol 4; 1,3-pentanediol 1; 2-methyl-1,2-propanediol 5 |
| 4 | γ-butyrolactone | 5 | 150 | >99 | 1,4-butanediol 92; 1-butanol 8 |
| 5 | γ-valerolactone | 5 | 150 | 91 | 1,4-pentanediol 89; 2-pentanol 5 |
| 6 | δ-valerolactone | 5 | 130 | >99 | 1,5-pentanediol 93; 1-pentanol 3 |
| 7 | ε-caprolactone | 5 | 130 | >99 | 1,6-hexanediol 91; 1-hexanol 7 |

Example 8

The same procedure as in Example 5 was performed except for changing the reaction temperature to 130° C. The results are shown in Table 2 below.

Example 9 (Preparation of Catalyst: Co-Impregnation Method)

A catalyst [Pt—Mo/₂ZrO, amount of Pt supported: 4 wt. %, amount of Mo supported: 0.485 wt. %, Mo/Pt (molar ratio)=0.25] was prepared in the same manner as in Example 1 except that the support shown in Table 2 below was used instead of hydroxyapatite.

The same procedure as in Example 8 was performed except that the catalysts prepared were used. The results are summarized as shown in Table 2 below:

Comparative Examples 1 to 7 (Preparation of Catalyst: Co-Impregnation Method)

Catalysts were prepared in the same manner as in Example 1 except that the supports shown in Table 2 below were used instead of hydroxyapatite.

The same procedure as in Example 8 was performed except that the catalysts prepared were used. The results are summarized as shown in Table 2 below:

[Chem. 4]

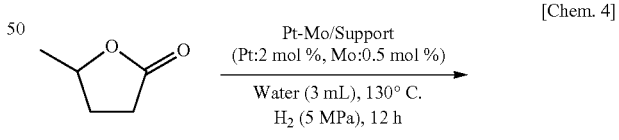

$$\xrightarrow[\text{H}_2\text{ (5 MPa), 12 h}]{\substack{\text{Pt-Mo/Support} \\ \text{(Pt:2 mol \%, Mo:0.5 mol \%)} \\ \text{Water (3 mL), 130° C.}}}$$

1 mmol

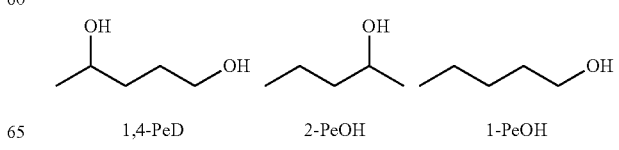

1,4-PeD    2-PeOH    1-PeOH

TABLE 2

| | Support | Conversion (%) | Yield (%) 1,4-PeD | Yield (%) 2-PeOH | Yield (%) 1-PeOH | 1,4-PeD Selectivity (%) |
|---|---|---|---|---|---|---|
| Example 8 | HAP | 60 | 54 | 3 | <1 | 90 |
| Example 9 | $ZrO_2$ | 63 | 62 | 4 | <1 | 98 |
| Comparative example 1 | $SiO_2$ | 97 | 67 | 20 | 1 | 69 |
| Comparative example 2 | $TiO_2$ | 95 | 50 | 31 | <1 | 53 |
| Comparative example 3 | H-β | 96 | 65 | 21 | 1 | 68 |
| Comparative example 4 | USY | 97 | 67 | 20 | 1 | 69 |
| Comparative example 5 | $MoO_3$ | 73 | 57 | 4 | <1 | 78 |
| Comparative example 6 | γ-$Al_2O_3$ | 29 | 16 | 11 | 0 | 55 |
| Comparative example 7 | MgO | 70 | <1 | <1 | 0 | <1.4 |

The supports used are as described below.
HAP: Hydroxyapatite, available from Wako Pure Chemical Industries, Ltd.
$ZrO_2$: Available from Wako Pure Chemical Industries, Ltd.
$SiO_2$: FUJI SILYSIA CHEMICAL LTD.
$TiO_2$: Reference catalyst, the Catalysis Society of Japan, JRC TIO-4
H-β: β type zeolite, reference catalyst, the Catalysis Society of Japan, JRC-Z-B25(1)
USY: USY type zeolite, available from N. E. Chemcat Corporation
$MoO_3$: Available from Wako Pure Chemical Industries, Ltd.
γ-$Al_2O_3$: AC-11, available from Sumitomo Chemical Co., Ltd.
MgO: Available from Ube Industries, Ltd.

It can be seen from Table 2 that by using the catalysts prepared in Examples to hydrogenate the lactone, the corresponding polyol can be produced at a selectivity of at least 90%.

Meanwhile, when the catalysts prepared in Comparative Examples were used instead of the catalysts prepared in Examples, selectivity of the polyol was significantly decreased.

Examples 10 and 11

The same procedure as in Example 8 was performed except for changing the reaction time as described in the table below. The results are summarized as shown in Table 3 below:

Examples 12 and 13

The same procedure as in Example 9 was performed except for changing the reaction time as described in the table below. The results are summarized as shown in Table 3 below:

Comparative Examples 8 and 9

The same procedure as in Comparative Example 1 was performed except for changing the reaction time as described in the table below. The results are summarized as shown in Table 3 below:

Comparative Examples 10 and 11

The same procedure as in Comparative Example 2 was performed except for changing the reaction time as described in the table below. The results are summarized as shown in Table 3 below:

TABLE 3

| | Support | Time (h) | Conversion (%) | Yield (%) 1,4-PeD | Yield (%) 2-PeOH | Yield (%) 1-PeOH | 1,4-PeD Selectivity (%) |
|---|---|---|---|---|---|---|---|
| Example 8 | HAP | 12 | 60 | 54 | 3 | <1 | 90 |
| Example 10 | | 24 | 78 | 72 | 4 | <1 | 92 |
| Example 11 | | 36 | 99 | 86 | 5 | <1 | 87 |
| Example 9 | $ZrO_2$ | 12 | 63 | 62 | 4 | <1 | 98 |
| Example 12 | | 24 | 91 | 82 | 5 | <1 | 90 |
| Example 13 | | 36 | 98 | 91 | 4 | <1 | 93 |
| Comparative example 8 | $SiO_2$ | 6 | 96 | 65 | 21 | 1 | 68 |
| Comparative example 1 | | 12 | 97 | 67 | 20 | 1 | 69 |
| Comparative example 9 | | 36 | >99 | 3 | 18 | 2 | <3 |
| Comparative example 10 | $TiO_2$ | 6 | 59 | 30 | 15 | <1 | 51 |
| Comparative example 2 | | 12 | 95 | 50 | 31 | <1 | 53 |
| Comparative example 11 | | 36 | 100 | 32 | 30 | 3 | 33 |

It can be seen from Table 3 that, in the cases where the catalysts prepared in Examples were used, when the reaction time was extended, the conversion ratio of the substrate can be improved without reducing the selectivity of the corresponding polyol.

Meanwhile, in the cases where the catalysts prepared in Comparative Examples were used instead of the catalysts prepared in Examples, although the conversion ratio of the substrate was improved when the reaction time was extended, the selectivity of the polyol was reduced. This was because in Comparative Examples, the intramolecular dehydration reaction of 1,4-pentanediol produced was promoted by the catalysts, and 2-methyltetrahydrofuran was produced as a by-product.

Example 14 (Preparation of Catalyst: Sequential Impregnation Method)

0.088 g of $(NH_4)_6Mo_7O_{24} \cdot 4H_2O$ was dissolved in 50 mL of water to prepare Solution (1).

Under room temperature (25° C.), 1 g of $ZrO_2$ was immersed in Solution (1) for 4 hours; after that, the resulting product was retrieved from Solution (1), and water was distilled off in a rotary evaporator under reduced pressure. This resulted in a powder. The prepared powder was then calcined in an air atmosphere in a muffle furnace at 500° C. for 3 hours. This resulted in $Mo/ZrO_2$.

0.0898 g of $H_2PtCl_6$ was dissolved in 50 mL of water to prepare Solution (2).

Under room temperature (25° C.), the resulting $Mo/ZrO_2$ was immersed in Solution (2) for 4 hours; after that, the resulting product was retrieved from Solution (2), and water was distilled off in a rotary evaporator under reduced pressure. This resulted in a powder. The prepared powder was then calcined in an air atmosphere in a muffle furnace at 500° C. for 3 hours. This resulted in a catalyst [$Pt/Mo/ZrO_2$, amount of Pt supported: 4 wt. %, amount of Mo supported: 0.485 wt. %, Mo/Pt (molar ratio)=0.25].

Example 15

The same procedure as in Example 9 was performed except that the catalyst prepared in Example 14 was used. The results are summarized and shown in Table 4 below.

Comparative Examples 12 and 13

The same procedure as in Example 9 was performed except for changing the catalyst as described in the table below. The results are summarized and shown in Table 4 below.

TABLE 4

|  |  | Conversion | Yield (%) | | | 1,4-PeD Selectivity |
|---|---|---|---|---|---|---|
|  | Cat. | (%) | 1,4-PeD | 2-PeOH | 1-PeOH | (%) |
| Example 9 | Pt—Mo/ZrO$_2$ | 63 | 62 | 4 | <1 | 98 |
| Example 15 | Pt/Mo/ZrO$_2$ | 70 | 63 | 4 | 0 | 90 |
| Comparative example 12 | Pt/ZrO$_2$ | 12 | 1 | <1 | 0 | 8.3 |
| Comparative example 13 | Mo/ZrO$_2$ | 0 | 0 | 0 | 0 | 0 |

Examples 16 to 18 (Preparation of Catalyst: Sequential Impregnation Method)

Catalysts [$Pt/Mo/ZrO_2$, amount of Pt supported: 4 wt. %] were prepared in the same manner as in Example 14 except that the concentration of $(NH_4)_6Mo_7O_{24} \cdot 4H_2O$ in Solution (1) was changed.

The same procedure as in Example 15 was performed except that the catalysts prepared were used. The results are summarized and shown in Table 5 below.

TABLE 5

|  | Mo (wt %) | Mo/Pt (mol/mol) | Conversion (%) | Yield (%) | | | 1,4-PeD Selectivity (%) |
|---|---|---|---|---|---|---|---|
|  |  |  |  | 1,4-PeD | 2-PeOH | 1-PeOH |  |
| Example15 | 0.5 | 0.25 | 70 | 63 | 4 | 0 | 90 |
| Example16 | 0.75 | 0.375 | >99 | 87 | 6 | <1 | 88 |
| Example17 | 1 | 0.5 | 80 | 75 | 4 | <1 | 94 |
| Example18 | 1.5 | 0.75 | 78 | 70 | 3 | <1 | 90 |

Example 19 (Preparation of Catalyst: Co-Impregnation Method)

A catalyst [Pt—Mo/ZrO$_2$, amount of Pt supported: 4 wt. %, amount of Mo supported: 0.75 wt. %, Mo/Pt (molar ratio)=0.375] was prepared in the same manner as in Example 1 except that the amount of (NH$_4$)$_6$Mo$_7$O$_{24}$·4H$_2$ was changed.

Examples 20 to 22

The same procedure as in Example 2 was performed except that: 1 mmol of γ-butyrolactone was used as the substrate; the catalyst prepared in Example 16 [Pt/Mo/ZrO$_2$, amount of Pt supported: 4 wt. %, amount of Mo supported: 0.75 wt. %, Mo/Pt (molar ratio)=0.375] or the catalyst prepared in Example 19 [Pt—Mo/ZrO$_2$, amount of Pt supported: 4 wt. %, amount of Mo supported: 0.75 wt. %, Mo/Pt (molar ratio)=0.375] was used as the catalyst; and the reaction time was changed as described in the table below. The results are summarized and shown in Table 6 below.

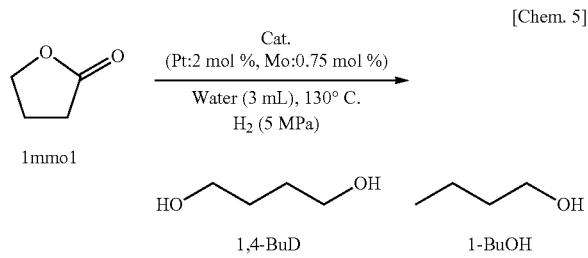

[Chem. 5]

TABLE 6

| Cat. (Pt: 4 wt % Mo: 0.75 wt %) | | Time (h) | Conversion (%) | Yield (%) | | 1,4-BuD Selectivity (%) |
|---|---|---|---|---|---|---|
| | | | | 1,4-BuD | 1-BuOH | |
| Example20 | Pt/Mo/ZrO$_2$ | 4 | >99 | 88 | 11 | 89 |
| Example21 | Pt/Mo/ZrO$_2$ | 6 | 97 | 86 | 9 | 87 |
| Example22 | Pt—Mo/ZrO$_2$ | 12 | >99 | 91 | 8 | 92 |

Examples 23 to 25

The same procedure as in Example 2 was performed except that: 1 mmol of δ-caprolactone was used as the substrate; the catalyst prepared in Example 16 [Pt/Mo/ZrO$_2$, amount of Pt supported: 4 wt. %, amount of Mo supported: 0.75 wt. %, Mo/Pt (molar ratio)=0.375] or the catalyst prepared in Example 19 [Pt—Mo/ZrO$_2$, amount of Pt supported: 4 wt. %, amount of Mo supported: 0.75 wt. %, Mo/Pt (molar ratio)=0.375] was used as the catalyst; and the reaction time was changed as described in the table below. The results are summarized and shown in Table 7 below.

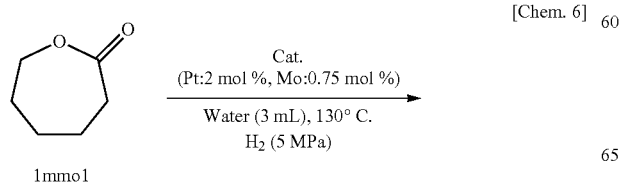

[Chem. 6]

TABLE 7

| Cat. (Pt: 4 wt %, Mo: 0.75 wt %) | | Time (h) | Conversion (%) | Yield (%) | | 1,6-HxD Selectivity (%) |
|---|---|---|---|---|---|---|
| | | | | 1,6-HxD | 1-HxOH | |
| Example23 | Pt/Mo/ZrO$_2$ | 4 | 99 | 85 | 10 | 86 |
| Example24 | Pt/Mo/ZrO$_2$ | 6 | >99 | 93 | 13 | 94 |
| Example25 | Pt—Mo/ZrO$_2$ | 12 | >99 | 93 | 10 | 94 |

It can be seen from Tables 6 and 7 that, the catalysts prepared by the sequential impregnation method had higher activity than the catalysts prepared by the co-impregnation method. Furthermore, it was found that, compared to when using a catalyst prepared by the co-impregnation method, lactone can be hydrogenated in a shorter amount of time when using a catalyst prepared by the sequential impregnation method.

To summarize the above, configurations and variations according to an embodiment of the present invention will be described below.

[1] A method for producing an alcohol, the method including hydrogenating a substrate lactone represented by Formula (1), in the presence of a catalyst, to produce an alcohol represented by Formula (2), wherein the catalyst comprises:
   metal species including M$_1$ and M$_2$; and
   a support supporting the metal species, and
   wherein
   M$_1$ is rhodium, platinum, ruthenium, iridium, or palladium;
   M$_2$ is tin, vanadium, molybdenum, tungsten, or rhenium; and
   the support is hydroxyapatite, fluorapatite, hydrotalcite, or ZrO$_2$.

[2] The method for producing an alcohol according to [1], wherein the amount of M$_1$ (in terms of metal) is from 1 to 50 wt. % of the weight of the support.

[3] The method for producing an alcohol according to [1] or [2], wherein the amount of M$_2$ (in terms of metal) is from 0.01 to 20 wt. % of the weight of the support.

[4] The method for producing an alcohol according to any one of [1] to [3], wherein the catalyst contains M$_1$ and M$_2$ as metal species in a ratio of from 0.05 to 1 mol of M$_2$ per 1 mol of M$_1$.

[5] The method for producing an alcohol according to any one of [1] to [4], wherein the supported amount of metal species besides M$_1$ and M$_2$ is no more than 70 mol % of the total supported amount of M$_1$ and M$_2$.

[6] The method for producing an alcohol according to any one of [1] to [5], wherein M$_1$ is platinum, ruthenium, iridium, or palladium.

[7] The method for producing an alcohol according to any one of [1] to [5], wherein M$_1$ is platinum, ruthenium, or iridium.

[8] The method for producing an alcohol according to any one of [1] to [5], wherein M$_1$ is platinum, ruthenium, or palladium.

[9] The method for producing an alcohol according to any one of [1] to [5], wherein $M_1$ is platinum, iridium, or palladium.

[10] The method for producing an alcohol according to any one of [1] to [5], wherein $M_1$ is platinum or palladium.

[11] The method for producing an alcohol according to any one of [1] to [5], wherein $M_1$ is platinum or iridium.

[12] The method for producing an alcohol according to any one of [1] to [11], wherein $M_2$ is vanadium, molybdenum, tungsten, or rhenium.

[13] The method for producing an alcohol according to any one of [1] to [11], wherein $M_2$ is vanadium, molybdenum, or tungsten.

[14] The method for producing an alcohol according to any one of [1] to [11], wherein $M_2$ is molybdenum, tungsten, or rhenium.

[15] The method for producing an alcohol according to any one of [1] to [11], wherein $M_2$ is vanadium, molybdenum, or rhenium.

[16] The method for producing an alcohol according to any one of [1] to [11], wherein $M_2$ is molybdenum or tungsten.

[17] The method for producing an alcohol according to any one of [1] to [16], wherein the support is hydroxyapatite or fluorapatite.

[18] The method for producing an alcohol according to any one of [1] to [16], wherein the support is hydroxyapatite or hydrotalcite.

[19] The method for producing an alcohol according to any one of [1] to [16], wherein the support is hydroxyapatite.

[20] The method for producing an alcohol according to any one of [1] to [16], wherein the support is $ZrO_2$.

[21] The method for producing an alcohol according to any one of [1] to [20], wherein R in Formula (1) above is a divalent aliphatic hydrocarbon group.

[22] The method for producing an alcohol according to any one of [1] to [20], wherein the lactone represented by Formula (1) above is a lactone having a 3- to 12-membered ring.

[23] The method for producing an alcohol according to any one of [1] to [20], wherein the lactone represented by Formula (1) above is a lactone having a 3-membered ring, or a lactone having a 4-membered ring, or a lactone having a 6-membered ring.

[24] The method for producing an alcohol according to any one of [1] to [23], wherein an amount of the catalyst in terms of the metal $M_1$ is from 0.01 to 30 mol % of the substrate.

[25] The method for producing an alcohol according to any one of [1] to [24], wherein a hydrogenation reaction is performed in the presence of water.

[26] The method for producing an alcohol according to any one of [1] to [25], wherein an amount of an organic solvent used is not greater than 50 wt. % of the amount of water used.

[27] The method for producing an alcohol according to any one of [1] to [26], wherein a selectivity of the alcohol represented by Formula (2) in the total amount of reaction products is not less than 70% at the time when a conversion ratio of the lactone represented by Formula (1) reaches not less than 90%.

[28] A hydrogenation catalyst for lactones that is used to hydrogenate a lactone to prepare a corresponding alcohol, in which the hydrogenation catalyst includes $M_1$ and $M_2$ described below, which serve as metal species, supported on a support described below.

($M_1$): rhodium, platinum, ruthenium, iridium or palladium ($M_2$): tin, vanadium, molybdenum, tungsten or rhenium (Support): hydroxyapatite, fluorapatite, hydrotalcite or $ZrO_2$

[29] A method for producing a catalyst, wherein the catalyst is used to hydrogenate a lactone to prepare a corresponding alcohol and is prepared by having the metal species $M_1$ and $M_2$ described below supported on a support described below.

($M_1$): rhodium, platinum, ruthenium, iridium or palladium ($M_2$): tin, vanadium, molybdenum, tungsten or rhenium (Support): hydroxyapatite, fluorapatite, hydrotalcite or $ZrO_2$.

[30] Use of a catalyst in an application where a lactone is hydrogenated to prepare a corresponding alcohol, wherein the catalyst comprising:

metal species including $M_1$ and $M_2$; and a support supporting the metal species, wherein:

$M_1$ is rhodium, platinum, ruthenium, iridium, or palladium;

$M_2$ is tin, vanadium, molybdenum, tungsten, or rhenium, and the support is hydroxyapatite, fluorapatite, hydrotalcite, or $ZrO_2$.

INDUSTRIAL APPLICABILITY

According to the production method in an embodiment of the present invention, an alcohol can be efficiently and selectively produced from a lactone under mild conditions in a one-step manner using water, which is environmentally friendly, as a solvent. Therefore, the production method according to an embodiment of the present invention is useful as a method for producing alcohol industrially.

The invention claimed is:

1. A catalyst comprising:

metal species including $M_1$ and $M_2$ in a ratio of from 0.3 to 0.8 mol of $M_2$ per 1 mol of $M_1$; and a support supporting the metal species, wherein:

$M_1$ is platinum;

$M_2$ is molybdenum; and the support $ZrO_2$, wherein the catalyst is a catalyst prepared using a sequential impregnation method in which $M_2$ is first supported on the support and then $M_1$ is supported on the support, and wherein the catalyst is used to hydrogenate a lactone to form a corresponding alcohol.

2. A method for producing an alcohol, the method including hydrogenating a substrate lactone represented by Formula (1), in the presence of a catalyst, to produce an alcohol represented by Formula (2),

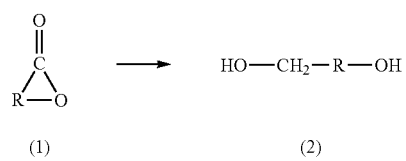

where R represents a divalent hydrocarbon group which may have a hydroxyl group, wherein the catalyst comprises:

metal species including $M_1$ and $M_2$ in a ratio of from 0.3 to 0.8 mol of $M_2$ per 1 mol of $M_1$; and a support supporting the metal species, and wherein $M_1$ is platinum;

$M_2$ is molybdenum; and the support is $ZrO_2$, wherein the catalyst is a catalyst prepared using a sequential impregnation method in which $M_2$ is first supported on the support and then $M_1$ is supported on the support.

3. The method for producing an alcohol according to claim 2, wherein the catalyst contains $M_1$ and $M_2$ as metal species in a ratio of from 0.3 to 0.6 mol of $M_2$ per 1 mol of $M_1$.

4. The method for producing an alcohol according to claim 2, wherein an amount of the catalyst in terms of the metal $M_1$ is from 0.01 to 30 mol % of the substrate.

5. The method for producing an alcohol according to claim 2, wherein the hydrogenation reaction is performed in the presence of water.

6. The method for producing an alcohol according to claim 2, wherein an amount of $M_1$ in terms of metal is from 1 to 50 wt. % of the weight of the support.

7. The method for producing an alcohol according to claim 2, wherein an amount of $M_2$ in terms of metal is from 0.01 to 20 wt. % of the weight of the support.

8. The method for producing an alcohol according to claim 2, wherein an amount of metal species other than $M_1$ and $M_2$ is no more than 70 mol % of the total amount of $M_1$ and $M_2$.

9. The method for producing an alcohol according to claim 2, wherein the lactone represented by Formula (1) is a lactone having a 3- to 12-membered ring.

10. The method for producing an alcohol according to claim 2, wherein the hydrogenation reaction is performed in the presence of water and an organic solvent, and wherein the organic solvent is used in an amount not greater than 50 wt. % of the amount of water.

11. The method for producing an alcohol according to claim 2, wherein a selectivity of the alcohol represented by Formula (2) in the total amount of reaction products is not less than 70% at the time when a conversion ratio of the lactone represented by Formula (1) reaches not less than 90%.

* * * * *